(12) United States Patent
Girndt

(10) Patent No.: US 8,214,161 B2
(45) Date of Patent: Jul. 3, 2012

(54) SYSTEM AND METHOD FOR DETECTING FLAWS IN WELDED TUBULARS

(76) Inventor: Richard J. Girndt, Spring, TX (US)

( * ) Notice: Subject to any disclaimer, the term of this patent is extended or adjusted under 35 U.S.C. 154(b) by 115 days.

(21) Appl. No.: 12/193,555

(22) Filed: Aug. 18, 2008

(65) Prior Publication Data

US 2009/0132181 A1 May 21, 2009

Related U.S. Application Data

(60) Provisional application No. 60/956,225, filed on Aug. 16, 2007.

(51) Int. Cl.
*G01N 29/04* (2006.01)

(52) U.S. Cl. ............... 702/39; 702/34; 702/38; 73/622; 73/628; 324/240

(58) Field of Classification Search ............ 702/34–39; 73/622, 628, 592, 598, 600, 632; 324/240
See application file for complete search history.

(56) References Cited

U.S. PATENT DOCUMENTS

| | | | | | |
|---|---|---|---|---|---|
| 4,192,986 | A | * | 3/1980 | Udagawa et al. | 219/137 R |
| 4,739,273 | A | * | 4/1988 | Petersen et al. | 324/242 |
| 6,373,245 | B1 | * | 4/2002 | Kwun et al. | 324/240 |
| 6,748,808 | B2 | * | 6/2004 | Lam et al. | 73/622 |
| 2008/0258719 | A1 | * | 10/2008 | Putman et al. | 324/240 |

OTHER PUBLICATIONS

Weld Seam Detector SND30, White Paper, Dec. 2001, Rev 1.3.
R2000 ECT40, White Paper, 1997-2009.
Steelcord-Inspection-System (SIS XP), White Paper, Jun. 23, 2005.

* cited by examiner

*Primary Examiner* — Drew A Dunn
*Assistant Examiner* — Hien X Vo
(74) *Attorney, Agent, or Firm* — Fulbright & Jaworski, LLP

(57) ABSTRACT

The system provides first and second sensor assemblies and processor that work in cooperation to detect flaws in welded tubulars. The first sensor detects and provides an indication of the weld line to the processor, which analyzes the indication and determines the approximate location of the weld line along the tubular. The processor then transmits a signal to the second sensor assembly, which is preferably mounted on an automatic positioning apparatus. In response to the signal, the automatic positioning apparatus adjusts and readjusts the position of the second sensor assembly into proximity with the weld line to search for flaws in the tubular.

20 Claims, 7 Drawing Sheets

SYSTEM AND METHOD FOR DETECTING FLAWS IN WELDED TUBULARS

CROSS-REFERENCE TO RELATED APPLICATIONS

This utility patent application claims priority to U.S. Provisional Patent Application Ser. No. 60/956,225, filed Aug. 16, 2007, the contents of which are incorporated by reference herein in their entirety.

TECHNICAL FIELD

The present invention generally relates to methods and apparatus for inspecting tubulars, and more specifically, but not by way of limitation, to methods and apparatus for ultrasonic detection of flaws in welded down hole tubulars.

BACKGROUND OF THE INVENTION

Oil and gas drilling companies subject down hole tubulars to extreme pressure and temperatures in drilling operations, and as such, seek to use tubulars that are best suited for the environment in which they will be utilized and therefore not prone to failure under extreme conditions. Structural flaws or defects in a tubular are one characteristic that can cause a tubular to fail during use. Accordingly, tubular manufactures perform ultrasonic inspections alone or in a combination with other NDT disciplines, to test the structural integrity of tubulars, looking for flaws, before the tubulars are used in the field.

Electric Resistance Welded ("ERW") manufacturers form tubulars by shaping and welding a flat steel plate into a full length tubular product. This process leaves a weld scarf or bead along the weld line, which is trimmed from both the inside and outside surface of the tubular. Although the processes for trimming the tubular's outside surface produces a near flush condition, often discernable only to the practiced eye, the processes for trimming tubular's inside surface leaves a definitive groove and edge along the weld line.

Accurately following the weld line and searching for structural flaws has historically presented substantial challenges to the tubular inspection industry including the two primary non-destructive testing ("NDT") disciplines—electromagnetic inspection and ultrasonic testing. Almost uniformly, ERW tubular inspectors are hampered with the problem of how to deal with the internal trim line left from removing the weld line flash or bead from the internal surface and the spurious non-relevant indications it can cause during NDT inspections. While the sharp weld line edge that results from the trimming process is detectable by both the electromagnetic and ultrasonic methods, in many cases, the reflectivity and/or flaw indications from the trimmed area cause false indications, not detrimental to the fitness for use, but are so severe that structural flaws in the weld or around the tubular are masked. Individuals responsible for quality control of ERW tubulars, for example, often inadvertently ignore true structural flaws by mistakenly assuming they were caused by the weld/trim. In addition, the length of the trim line and the resultant reflection (in the case of ultrasonic inspection), the flux leakage (in the case of electromagnetic inspection), and the variance in metallurgical properties (in the case of eddy current) often cause a spurious, non-relevant flaw indication that can mask the indications from actual flaws or defects. Existing inspection techniques therefore detract from the accuracy and reliability of the NDT processes.

Ultrasonic inspections apparatuses are most commonly mounted immediately in line behind the welder, where they can inspect the tubular's weld seam when it is in the 12 o'clock position. This practice is followed by most all ERW mills in order to comply with American Petroleum Institute ("API") specification. Ultrasonic tubular inspections are performed after the tubular product has cooled and been subjected to several post-welding processes that may negatively impact the final product's quality or fitness for use. Ultrasonic inspections also typically take place after the tubular is cut to length and the circumferential location of the full length weld is known.

It is a common practice to perform a second ultrasonic inspection as part of a separate, manual ultrasonic weld line inspection to provide an offline quality control measure. Manual inspection poses a unique technological problem in that the tubular's welded zone is difficult if not impossible to identify by visual inspection from the external surface.

During manual inspection, inspectors typically look on the inside surface of the tubular to locate depressions formed by flash trimming tools/operations. Manual inspection is both labor intensive and time consuming when considering the training required to locate the weld and manpower to roll the tubular to place the weld line into the correct position to be inspected by the ultrasonic inspection apparatuses. Additional problems arise in the manufacturing process because the weld seam is not always formed in a straight line down the longitudinal axis of the tubular. On small diameter tubulars, for example, the weld line can spiral more than 90 degrees from one end of the tubular to the other.

Once inspectors locate the weld line, they typically roll the weld to the 12 o'clock position then mark the weld line with a chalk line for visual identification. Inspectors typically apply the chalk line by "popping" a contrast colored chalk string along the weld line. This process is slow and labor intensive but is an accepted way of ensuring that inspectors can identify where/how to position the inspection "crab", so that it remains relatively centered on the weld line, during the inspection process. If the weld line spirals (e.g., wanders) down the tubular, inspectors make multiple passes with the inspection crab or trolley to trace the chalk line, resulting in increased inspection costs and job time. Another drawback with this method is that inspectors must walk the weld line "crab" from one end of the tubular to the other while dragging along the umbilical cord that connects the test head to the ultrasonic inspection electronics. The umbilical includes a number of co-axial cables and a water line, which makes it cumbersome.

Thread protectors often interfere with accurately locating the trim line as many types of protectors are "closed end", to seal the inside of the tubular and prevent damage to the threaded ends. The protective covers must be removed from the tubular to locate the internal trim line and accurately apply the chalk line. This process is both labor intensive and exposes the finished threads to debris, damage, and contamination. After ultrasonic inspection, the protective covers must be reattached after the inspection process to prevent damage or contamination of the tubular in later processes.

Tubular manufactures also face significant difficulty in efficiently tracking the weld line after the tubular is welded and cut to length. Manufactures often attempt to identify defective tubulars by applying paint stripes to the weld line, and then following the paint stripe with a video camera to track the weld and ultrasonically scan for flaws. Skilled technicians typically operate the video camera and visually search for slight differences on the outside surface of the tubular caused by the weld seam. Even for skilled technicians it is difficult to visually detect the slight differences on the outside surface of the tubular. As a result, the video method slows down productivity and diminishes efficiencies sought by high production steel mills. Paint stripes are typically permanent and not welcomed by ERW tubular manufacturers whose clients—end user oil and gas companies—perceive the painted weld zones as prone to failure during hydrostatic testing, or worse, under pressure down hole in the well bore. The paint line itself draws attention to the fact that this material is a welded product, which carries the stigma of a higher potential of failure in the welded area.

Tubular consumers prefer seamless tubulars in lieu of ERW in deep offshore wells. Seamless tubulars are stronger and more expensive. Typically, drill pipe tubulars are seamless due to the intense torque and pressure applied during the drilling process. Seamless tubulars most frequently fail on the tubular ends, rather than along the weld seam.

Another existing method for detecting tubular flaws utilizes mechanical means to inspect weld lines that spiral around the tubular. Mechanical weld tracking methods are used for spiral weld tubulars with an external protruding weld bead, rather than oil country ERW products, which have smooth external surfaces in the welded area.

Another existing method utilizes a pitch catch ultrasonic technique that relies on measuring the reflected ultrasonic energy with a second ultrasonic probe. This method uses two ultrasonic transducers located on the same side of the weld to measure the reflected energy from a weld defect. This method only provides a way to follow the weld after it is located visually and does not provide the ability to locate the weld.

Another existing inspection method attempts to detect different electromagnetic properties in the weld using the eddy current method. The eddy current method seeks to detect variations in the weld area, when compared to the entire tubular circumference. The problem with the eddy current method is that the weld line is commonly normalized or subject to heat treatment on the higher grades of ERW tubulars in order to ensure there is little or no difference between the parent plate steel and the weld, which render this method's reliability inconsistent and variable over the range of ERW products.

Another existing technology includes use of a phased arrays to ensure full inspection coverage of the weld zone when its location is not known. Such phased array systems must encircle the entire tubular, with the sensors programmed to alternately look clockwise and counterclockwise around the tubular, thus inspecting the weld where ever it is located. This method is not cost effective, as larger diameter (e.g., less than 13.375) Oil Country Tubular Goods ("OCTG") are likely to be manufactured by the ERW method, which increases the number of encircling phased array probes required to ensure complete surface coverage. Phased array technology does not attempt to locate the weld, and as a result, the transducers and electronics away from the weld are excess, are not needed for the test, resulting in unnecessary costs.

Embodiments of the present invention overcome the above and other problems inherent to existing tubular inspection technologies by using lower cost and more reliable inspection techniques disclosed herein. Embodiments of the present invention are primarily suited for detecting flaws in ferromagnetic material and in particular, in tubular goods such as pipes and well casing, but the disclosed embodiments may also be adapted to inspect other types of tubulars. For avoidance of doubt, the term "tubular" includes all forms of tubular goods, including structural shapes that range of small to infinite radius of curvature.

DETAILED DESCRIPTION OF THE INVENTION

Figure 1:
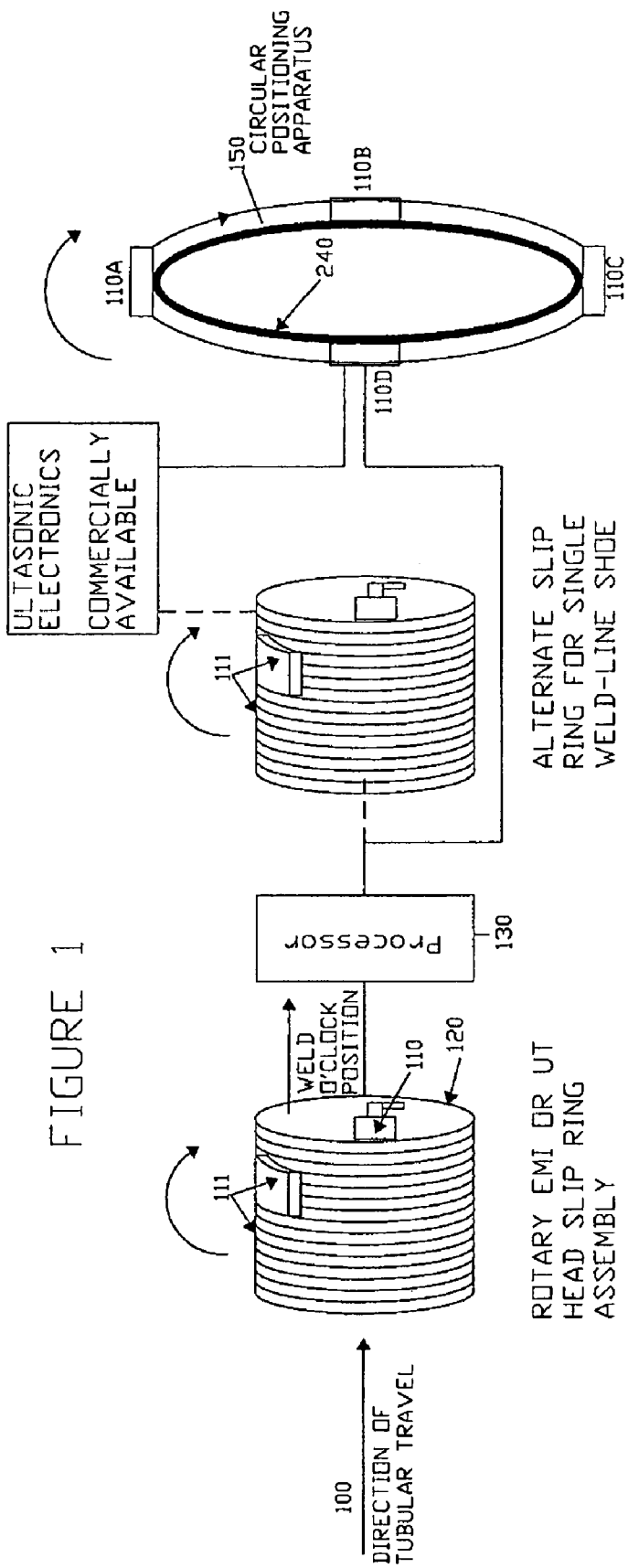
FIG. 1 shows an example embodiment of the system and method for detecting flaws in welded tubulars.

FIG. 1 shows an example diagram of the preferred system. The system includes a tubular conveyor that moves tubulars past a rotary head 120 fitted with a sensor 110 for detecting the tubular's weld line. The sensor revolves around the tubular on a rotary head 120 and through a slip ring assembly 111, with said slip ring assembly having a "brush box" contact device which collectively transfer data from a rotating device to a fixed data transfer cable or connection. As the tubular passes, the sensor generates data to indicate the location and shape of the weld line. The sensor then feeds the data to a processing device 130 that automatically positions the closest (or otherwise optimal) additional test shoe that contains sensors (e.g., 110A, 110B, 110C, or 110D) to track the weld line in search of nearby structural imperfections that may ultimately cause the tubular to fail during use.

The conveyor 100 preferably includes a series of "v" rollers (not shown) aligned on parallel axes transverse to the direction of conveyor flow. At least one of the rollers preferably tapers inward to hold tubulars by force of gravity. At least one of the rollers is also preferably motorized to move the tubulars axially through the system. In alternative embodiments, the conveyor comprises one or more belts that move the tubulars through the system.

As shown in FIG. 1, the conveyor first moves a tubular through rotary head 120, which is fitted with sensor 110. Sensor 110 is designed to identify the weld line and, optionally, also identify any structural flaws that exist in the tubular nearby or away from the weld line. Sensor 110 may comprise one or more flux leakage detectors that measure magnetic flux caused by flaws in the tubular. Alternatively, sensor 110 scans using the hall effect NDT method and also looks for the ring of flux cause by an anomaly or defect using the magnetic fields generated by the flux ring (not shown) rotating around the tubular. Sensor 110 also alternatively comprises one or more ultrasonic transducers that project ultrasonic waves through the wall of the tubular member and read the reflection of the ultrasonic waves.

Figure 2:
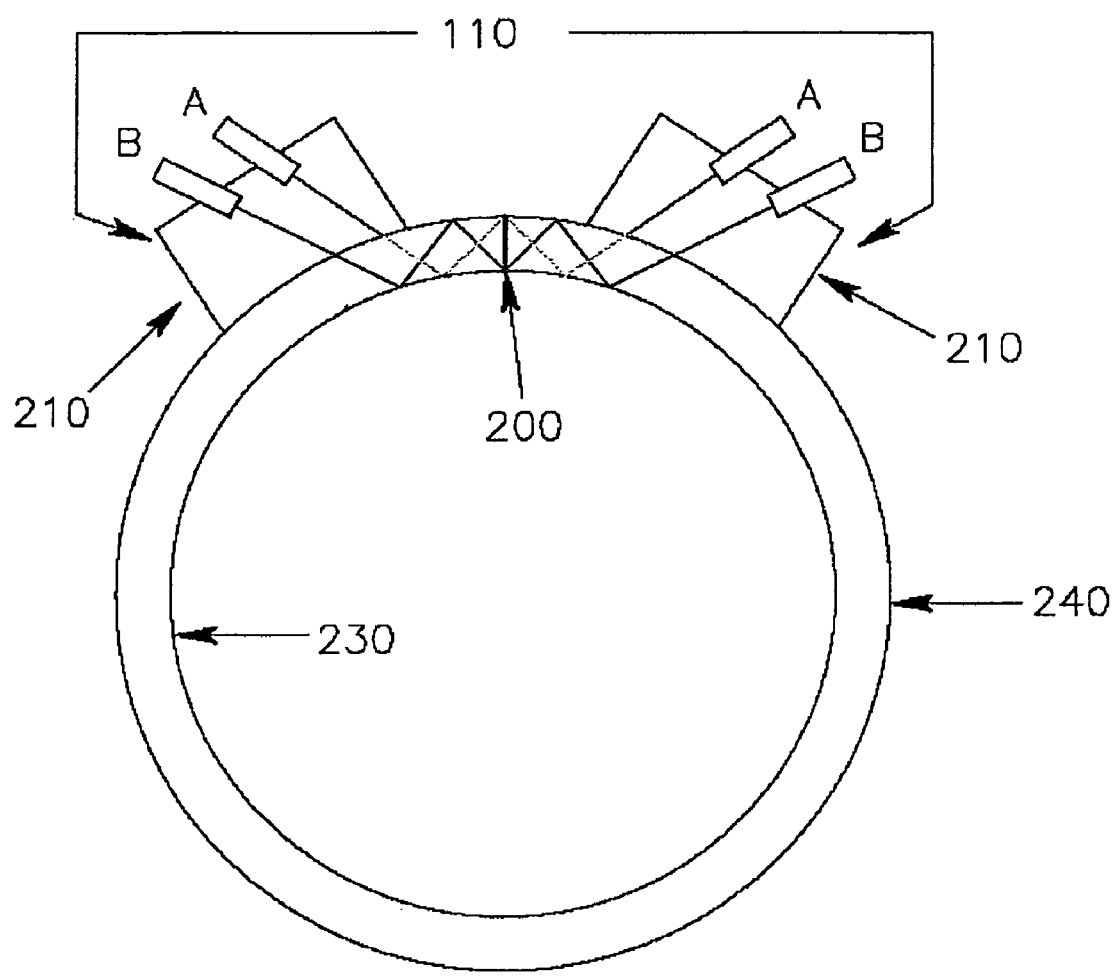
FIG. 2 shows an example ultrasonic sensor array for detecting flaws in welded tubulars.

FIG. 2 shows an example embodiment of an ultrasonic inspection shoe 110. The ultrasonic inspection shoe 110 depicted in FIG. 2 includes first 210 and second 220 probes. Each probe includes an array of ultrasonic transducers (groups A and B) which are positioned on either side of the weld line 200. One probe's array of transducers focus on the tubular's internal surface 230 (e.g., ID) and the other probe's array of transducers is trained on the tubular's outside surface 240 (e.g., OD). Although the ultrasonic beams projected by the transducers are depicted as straight lines in FIG. 2, one of ordinary skill in the art will appreciate that the effective beam area is actually approximately 80% to 85% of the transducer's crystal size. During inspection, the transducers maintain a relatively fixed distance from the weld line in order to ensure complete coverage of the inside surface and outside surface of the weld. The transducers shown in FIG. 2, may be any suitable transducer known in the art, or of the type disclosed in U.S. Pat. No. 7,293,461 to R. Girndt, hereby incorporated by reference in its entirety.

As depicted in FIG. 1, the tubular moves though the system along the conveyor while rotary head 120 passes over the tubular in a circular manner. This allows sensor 110 to can scan the tubular's OD and collect and report information about the tubular's weld line, such as location, thickness, length, internal contour, external contour, etc. Sensor 110 can also track the position of any weld line and any other pertinent information about the weld line or flaws.

To guide the tubular, centering pinch rollers guide the tube through the rotary slip ring 111 which is sized for the range of diameters common to OCTG material, and which rotates around the circumference of the tubular. The tubulars preferably have a diameter ranging from approximately 2⅜" to 13⅜", but may be smaller or larger diameter tubulars may be used as desired. In this arrangement, the tubular being inspected is preferably rotated at speeds of approximately 450 revolutions per minute to enable optimal performance of sensor 110. In this embodiment, the tubulars are preferably.

Those of skill in the art will appreciate that the system can be adjusted to inspect tubulars of any diameter traveling at any rotational speeds. Preferably, rotary head containing slip ring 120 is also fitted with contact wear shoes (not shown) so that tubulars can be inspected by the system when they are displaced (e.g., laterally) as they progress past the revolving head. However, contact shoes that accommodate far greater or lesser positional offset may be used as well.

As the sensor 110 scans a tubular, the sensor reports the collected inspection data to a processor 130. The processor 130 may be any suitable computing hardware or software capable of analyzing electronic data and issuing instructions. As shown in FIG. 1, the preferred processor is a programmable logic controller ("PLC") of the sort generally known in the art. Processor 130 processes the data collected by the weld line detector and, if desired, graphically displays such data. Processor 130 may also determine whether the collected data passes/fails predetermined quality control thresholds set by the operator according to industry standards or customer quality expectations. Alternatively, depending on the desired application and design, the processor may be configured to only track the weld line.

Data transmitted to the processor 130 preferably includes (among other information) a reoccurring signal comprising the circumferential position the weld line and any flaw(s). Such data is collected during each revolution of the sensor around the tubular flaw. It is acknowledged that the amplitude of signals derived from the weld line detector will vary depending on the quality of the internal trim line, the type of sensors employed, and the sensor settings. For example, if a sensor's flaw position tracking control is set to run "hot" or extremely sensitive tests, random non-relevant indications may be detected away from the trim line. The processor 130 is therefore programmed to filter out reoccurring and non-random flaw indications to accurately identify the weld line and flaws.

Based upon the location of the weld line identified by the processor 130, the processor preferably issues instructions to an automatic rotary positioning apparatus 150 which, in response to the instructions, positions a second test shoe 110 (shown in FIG. 2) to trace the tubular's weld line looking for flaws. It should be noted that in alternative embodiments the processor 130 may also issue instructions to the automatic positioning apparatus 150 to position the second sensor 110 over a portions of the tubular suspected of containing a structural flaw.

Figure 3:
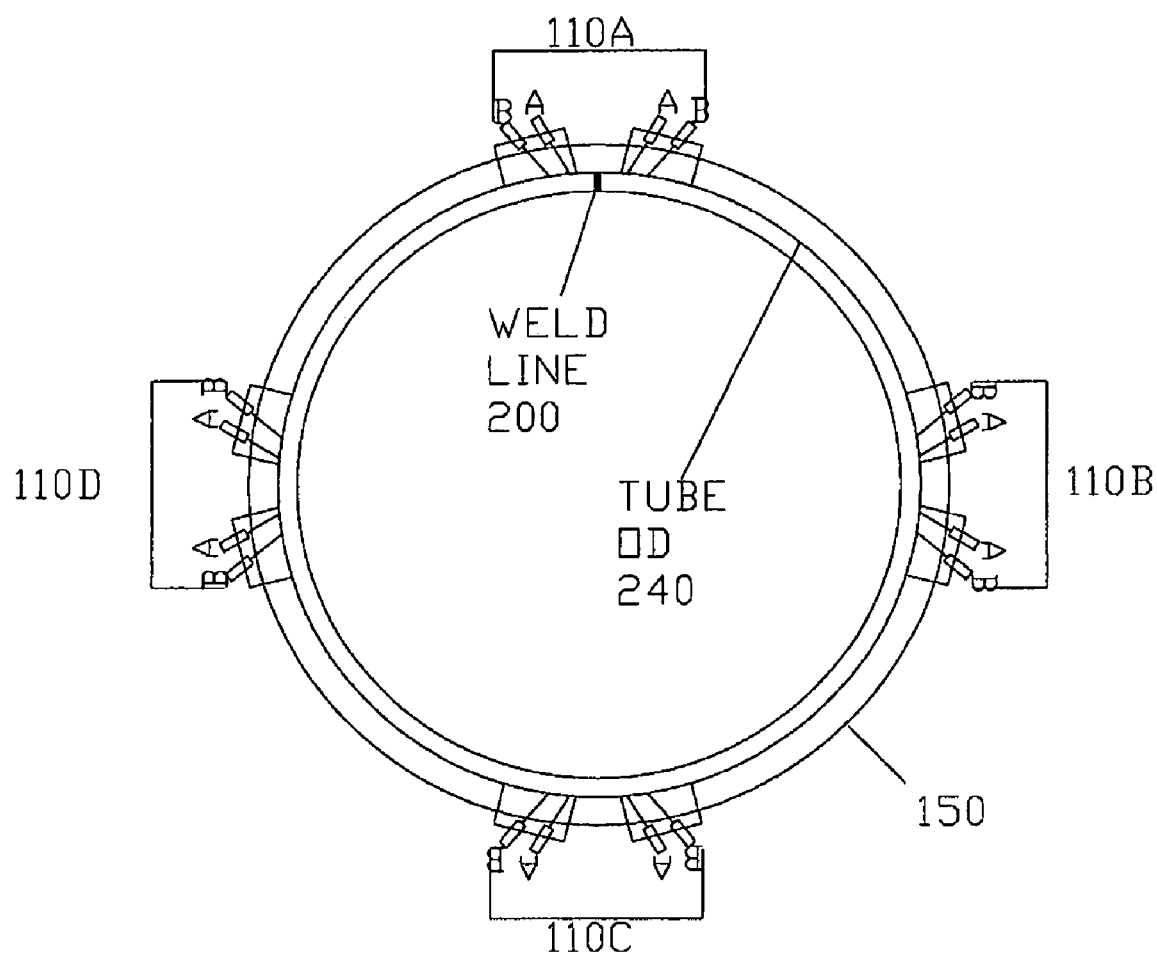
FIG. 3 shows an example of an automatic positioning apparatus fitted with four example sensor arrays.

FIG. 3 shows a preferred embodiment for higher volume inspections. In this embodiment, the processor 130 issues instructions to an automatic rotary positioning apparatus fitted with four inspection shoes each having a group of sensors 110A, 110B, 110C, and 110D. The automatic positioning apparatus includes a rotary head (not shown) that supports the four sensors, and electronics to carry out instructions from the processor 130. The automatic positioning apparatus also includes appropriate cogs, bearings and gears. In one embodiment the automatic positioning apparatus further includes a slip ring with rotary barrel, sensors and brushes, which are affixed to the rotary positioning device 150. Based upon locational information for the four independent sets of sensors and the tubular's weld line, the processor 130 determines which of sensors 110A, 110B, 110C, or 110D is closest to the weld line and activates this sensor for pulsing. The processor 130 from FIG. 1 has locational information about the tubular's weld line by processes carried out earlier by sensor 110 (depicted FIG. 1). By activating only the closest sensor for pulsing, this embodiment overcomes problem of redundant testing inherent to existing circular phased array systems, while reducing the associated costs of providing individual electronic that are in excess to what is need to perform the test.

FIG. 3 shows an example embodiment of the automatic positioning apparatus 150, which is fitted with four sensors 110A, 110B, 110C, and 110D. The sensors shown in FIG. 3 may analyze flux leakage, Hall effect, ultrasonic waves, or any other flaw detection technology known in the art. The sensors are preferably spaced proportionately around the rotary head. Although not show, in one embodiment the sensors carry a compression wave to monitor the characteristics of the trimming operation including depth of the depression due to trimming. Sensors may alternatively carry shear probe waves.

Figure 4:
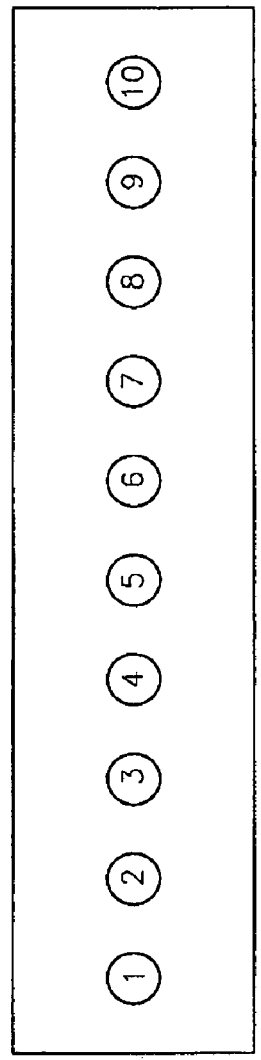
FIG. 4 shows an example inspection shoe common to electromagnetic and hall effect electromagnetic inspection, with a plurality of coils for detecting structural flaws in tubulars.

FIG. 4 shows another example sensor for detecting longitudinal flaws. The sensor may be part of an existing EMI unit. The sensor generally represents any of structures 110, 110A, 110B, 110C shown in FIGS. 1, 2, and 3. In one embodiment, a flux ring or rotary head (e.g., magnetic yoke) (shown in FIG. 1) impose an active transverse magnetic field on the portion of the tubular being inspected. If there is a structural flaw in the tubular, the magnetic coils of FIG. 4 numbered 1-10 detect flux leakage. The leakage detected by the coils provides an electrical input signal for the processor 130 to display, record and analyze to indicate the presence, location and extent of the structural flaw.

In an alternative embodiment, the magnetic coils number 1-10 in FIG. 4 represent solid state sensors for electromagnetically detecting flaws. It will be appreciated by those of skill in the art that, if the coils numbered 1-10 in FIG. 4 embody electromagnetic technology, the signal derived therefrom is transmitted to processor 130 to identify the location of the weld line and/or to determine the position of the closest downstream sensor.

Figure 5:
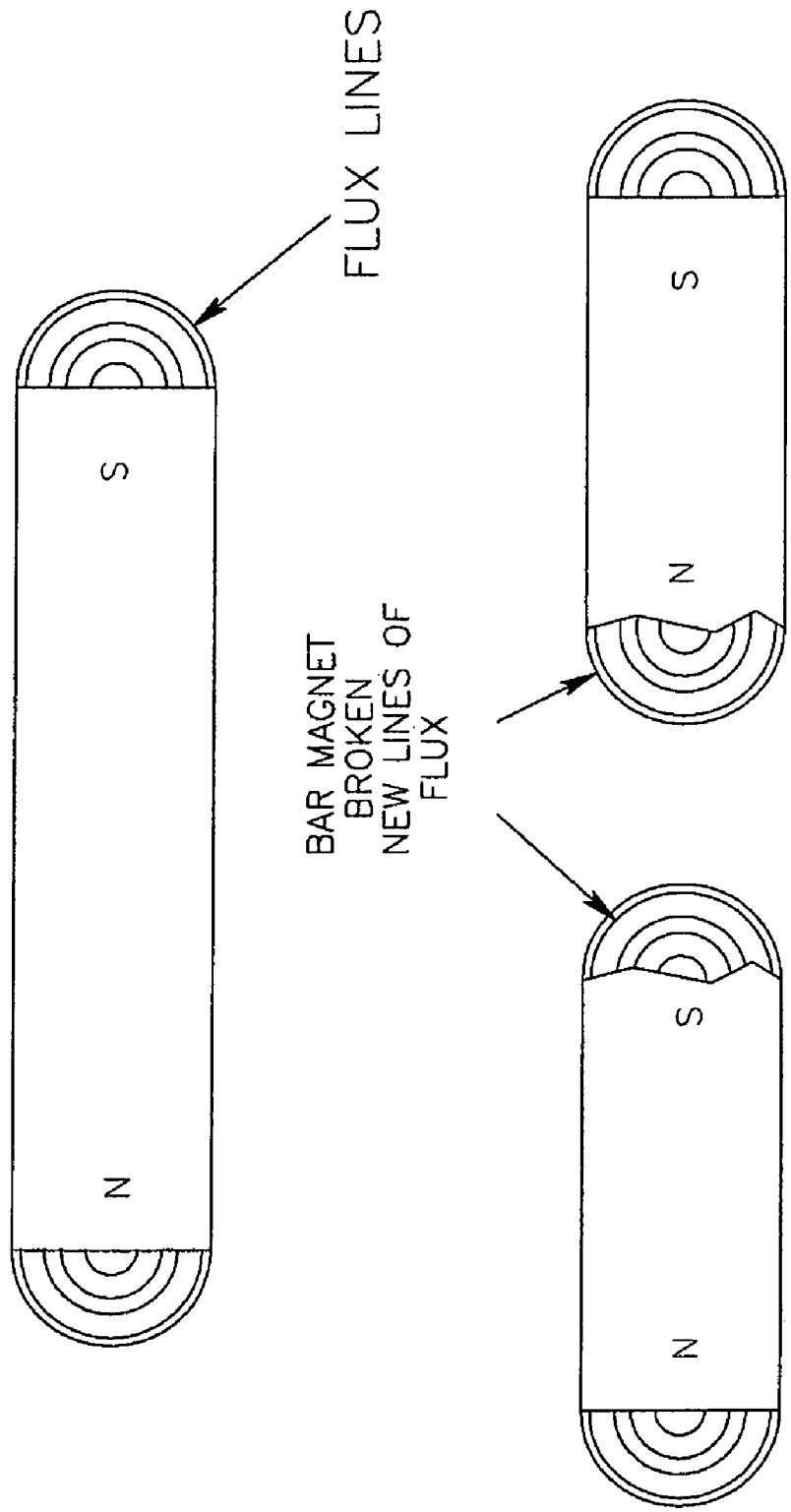
FIG. 5 shows example flux lines of a bar magnet.

FIG. 5 shows magnetic flux lines that Hall effect sensors 110 seeks to detect using Hall effect sensors, Electromagnetic sensing coils (and alternatively certain steel or eddy current probes) are rotated around the tubular while the tubular is magnetized to detect flux leakage from cracks or other longitudinally oriented flaws when using a transverse magnetic field. The flux leakage in the tubular are similar to the lines of flux at the north and south poles of a bar magnet. For example, as shown in FIG. 5, if a bar magnet is broken into two pieces, a new north and south pole are be created at the break, producing new areas of flux leakage. Similarly, when a tubular in sufficiently magnetized, a crack in a tubular product reacts by forming north and south pole detectable by sensors 110.

Figure 6:
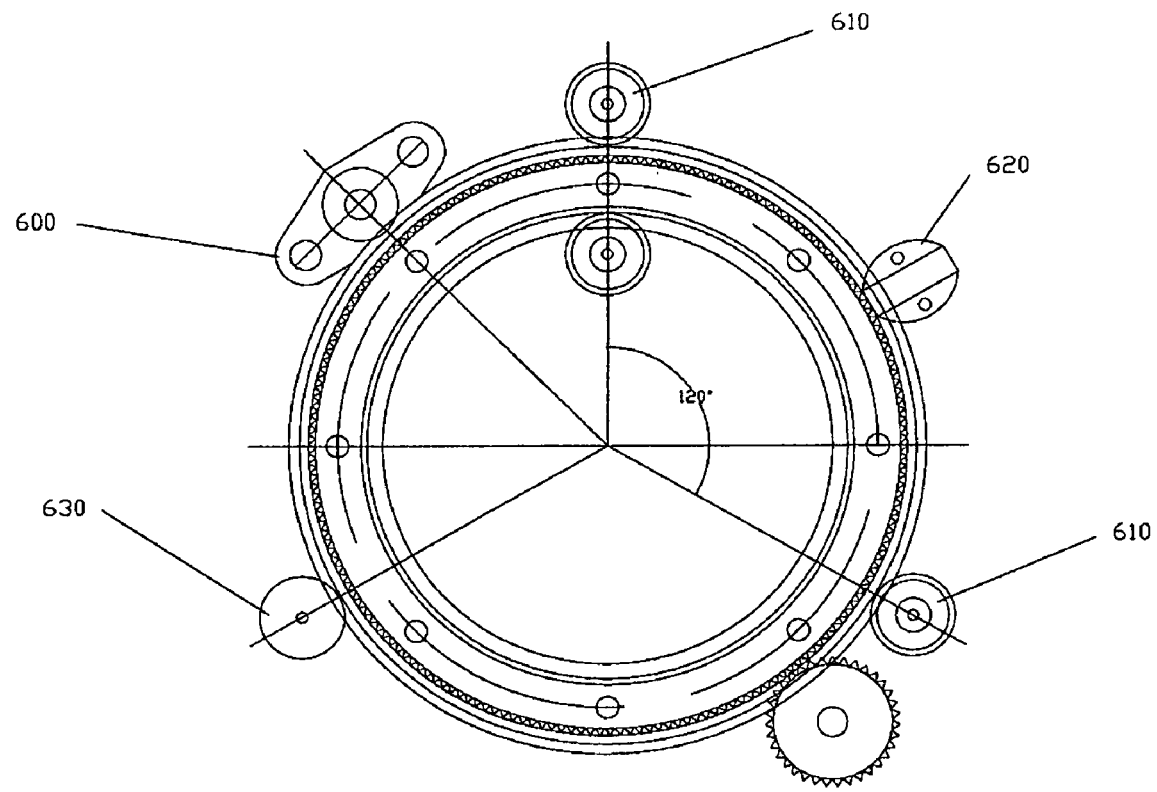
FIG. 6 shows an example rotary positioning apparatus.

FIG. 6 depicts and example rotary positioning apparatus, which includes an eccentric blind hole fixing bearing assembly 600 and eccentric bearing assembly 620. The slip ring also includes a lubricator 620, concentric bearing assemblies 610, and eccentric bearing assembly 630. One or more of the bearing assembly is adapted to received a signal from the processor 130 and, in response, position at least one sensor 110A, 110B, 110C, 110D in proximity with a tubular's weld line so that they sensor can inspect for flaws. One of skill in the art will appreciate that a single shoe mounted to a slip ring would may be substituted for the rotary positioning apparatus.

Figure 7:
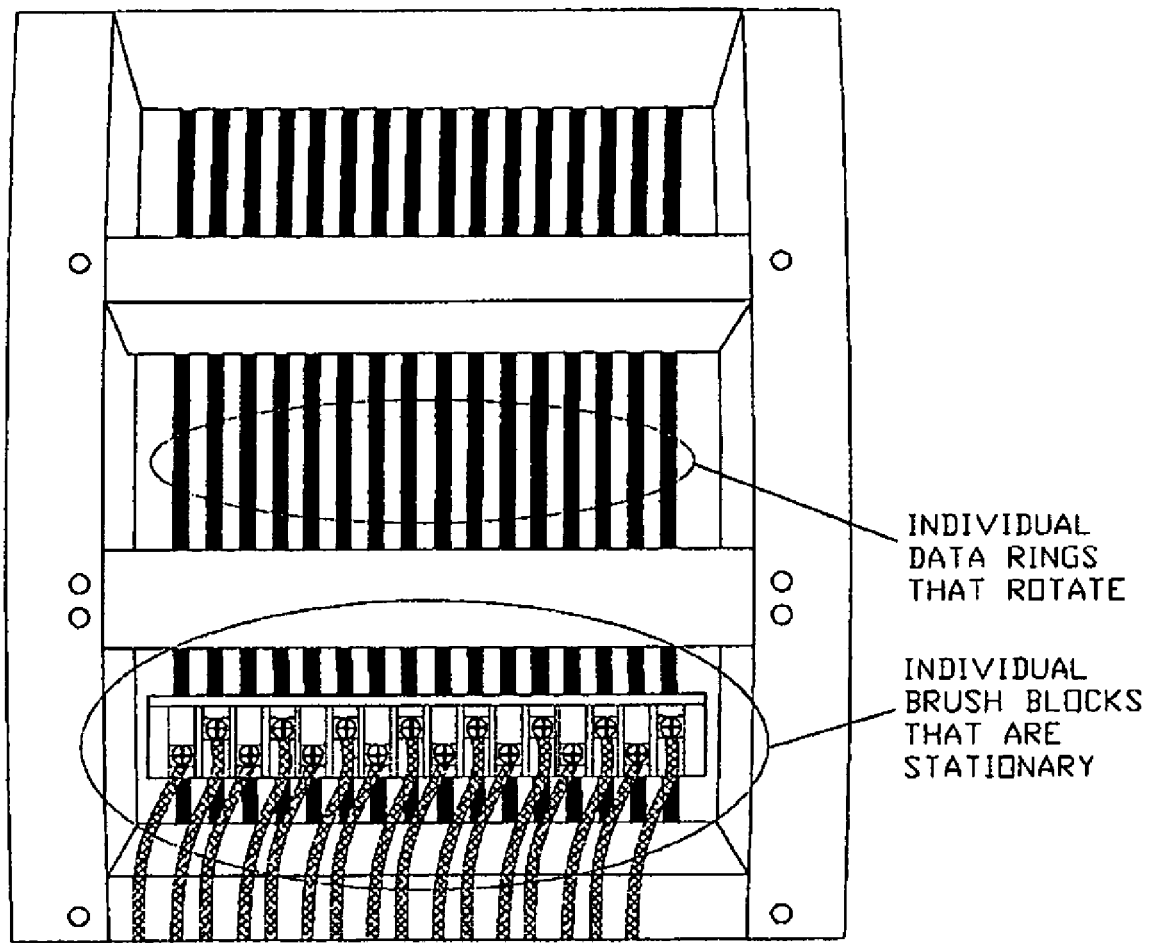
FIG. 7 shows an example slip ring.

FIG. 7 shows a slip ring used in embodiments of the present invention. The slip ring includes a plurality of individual rotating data rings. The slip rings also includes a plurality of stationary brush blocks. The of skill in the art will appreciate the additional structures and functionality that make up the slip ring shown in FIG. 4.

It should also be noted that the system described herein can be configured as an integrated stand alone piece of equipment. In another embodiment, the system described herein may be retrofitted to work with existing rotary electromagnetic or ultrasonic inspection apparatus in a tubular manufacture's production facility. To retrofit, the signal from existing sensors provide the positioning information of the weld line, thereby reducing the capital costs and increasing the performance of existing equipment. This feature saves time, uses existing resources, and reduces the need for secondary downstream weld line inspections.

As will be appreciated from the above disclosure, the system gathers information from two sets of sensors—one set of upstream sensors and one downstream. By feeding information from each of these sensors to the processor 130, where the data can be synchronized and compared, the system provides reliable and accurate information regarding any structural flaws. The upstream and downstream sensors may exit on separate structures, so long the sensors cooperate by relaying information to and from a central processor 130 to carry out coordinated inspections consistent with the embodiments herein.

Embodiments of the present invention disclosed herein overcome problems inherent to the prior art in a number of ways. The system no longer requires human input to locate and track the weld seam on ERW tubular. The tubular's weld line no longer needs to be positioned in any particular location, such as 12 o'clock, to ensure it's location, monitor visually, give ready access to the ultrasonic inspection head, or apply a paint or chalk line to follow the weld line with a "crab" or semi-automated inspection head. The system does not require multiple sensor passes to ensure a wandering or spiraling weld line has been inspected. Costly certified technical personnel are no longer needed to manually adjustment to the position of the weld line inspection sensor to compensate for the spiral of the weld line. The system archives data collected by the sensors to verify the sensors followed the weld line. Input signals readily available from existing mill equipment are used to position the head and accurately track and inspect the weld seam. The system is portable to meet stringent, secondary, end user specifications after the material has left the point of manufacture. Any site where the mill has axial transfer "V" style rollers will accommodate the machine. The system installs in existing mill production lines and does not detract from the quantity of tubular manufactured on a daily basis. The system keeps pace with the normal flow of the manufacturers operations. During subsequent inspections performed after threading, embodiments of the invention negate the need to pull the closed end thread protectors to visually locate the weld line. Embodiments leave the protectors in place and remove the risk of contaminating or damaging the thread compound applied underneath the protectors. The system provides for fast accurate inspection of welded tubulars using the ultrasonic method for the weld line inspection. A minimal investment is required to add to the life span of existing electromagnetic tubular inspection units by using the existing signal from a manufacturer's machine. The system can act as a stand alone weld inspection system or be mounted downstream from existing flux leakage EMI inspection units.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the inspection system and the methods described in the specification. As one will readily appreciate from the disclosure, user interfaces and methods presently existing or later to be developed that perform substantially the same function or achieve substantially the same result as the corresponding embodiments described herein may be utilized. Accordingly, the appended claims are intended to include within their scope such articles and methods.

What is claimed is:

1. A system for detecting tubular flaws comprising:
   at least one first sensor for scanning a tubular member and, upon detecting a weld line during a revolution, generating a signal representing the circumferential position of the weld line;
   a processor, electronically coupled to the first sensor, for receiving and analyzing the signal representing the circumferential position of the weld line to determine the location of the weld line on the tubular,
     wherein the processor is configured to transmit a signal representing the location of the weld line on the tubular;
   a positioning apparatus having at least one second sensor, the positioning apparatus electronically coupled to the processor, for receiving the signal representing the location of the weld line on the tubular and, in response, adjusting the second sensor's relative position closer to the tubular's weld line on the tubular to scan for flaws;
     wherein the positioning apparatus comprises a plurality of sensors and wherein the processor is configured to:
       to determine the position of the closest of said plurality of sensors to the weld line, and
       to activate said closest sensor to scan for flaws nearby or in the weld line on the tubular.

2. The system of claim 1, wherein the electromagnetic sensor comprises an electromagnetic sensor for detecting magnetic flux leakage of a tubular's weld line or a Hall effect sensor for detecting flux leakage of the tubular's weldline.

3. The system of claim 1, wherein the first sensor comprises an eddy current sensor for detecting different metallurgical properties of a tubular's weld line.

4. The system of claim 1, wherein the first sensor comprises an ultrasonics sensor for detecting ultrasonic reflectivity and amplitude waves of a tubular's weld line.

5. The system of claim 4 wherein the slip ring assembly comprises a plurality of rotating data rings and stationary brush blocks.

6. The system of claim 1, wherein the first sensor is coupled on a slip ring assembly.

7. The system of claim 1, wherein the processor comprises a programmable logic controller.

8. The system of claim 1, wherein the processor comprises and data processing device.

9. The system of claim 1, wherein the second sensor comprises at least one electromagnetic sensor for detecting magnetic flux leakage of a tubular's weld line.

10. The system of claim 1, wherein the at least one second sensor comprises at least one Hall effect sensor for detecting a voltage difference on opposite sides of the tubular's weld line.

11. The system of claim 1, wherein the second sensor comprises at least one eddy current sensor for detecting different metallurgical properties of a tubular's weld line.

12. The system of claim 1, wherein the second sensor comprises at least one ultrasonic sensor for detecting ultrasonic reflectivity and amplitude waves of a tubular's weld line.

13. The system of claim 1, wherein the second sensor is mounted on an automatic positioning apparatus formed by a slip ring assembly adapted to automatically adjust based upon the signal representing the location of the weld line.

14. The system of claim 13, wherein the automatic positioning device's slip ring assembly comprises a plurality of data rings and brush blocks.

15. The system of claim 1, wherein the second sensor is mounted on a rotary positioning device adapted to automatically adjust based upon the signal representing the location of the weld line.

16. A method for detecting tubular flaws comprising:
scanning the circumference of a tubular member with a first sensor assembly to detect the tubular's weld line;
sending a signal from the first sensor assembly to a processor upon detecting the tubular's weld line;
receiving and analyzing the signal at a processor to determine the location of the tubular's weld line,
wherein analyzing the signal at the processor comprises determining the closest sensor to the tubular's weld line among a plurality of sensors in the second sensor assembly;
transmitting the location of the tubular's weld line to a second sensor assembly; and
adjusting the second sensor assembly, based upon the location of the weld line, into proximity with the tubular's weld line to scan for flaws.

17. The method of claim 16 further comprising the step of pulsing the closest sensor in the second sensor assembly to search for flaws in the tubular.

18. The method of claim 16, wherein the step of adjusting the second sensor assembly comprises the step of controlling an automatic positioning apparatus, fitted with at least one ultrasonic sensor, to move into proximity with the tubular's weld line to search for flaws.

19. The method of claim 16, wherein scanning the circumference of the tubular member comprises rotating the first sensor around the circumference of the tubular or rotating the tubular circumferentially.

20. An apparatus for detecting tubular flaws comprising:
a first sensor for scanning a tubular member and, upon detecting a weld line, generating a signal representing the weld line;
a plurality of second sensors for detecting flaws in a tubular member; and
a processor, coupled to the first sensor and the second sensors, adapted to analyze the signal representing the weld line,
wherein the processor is configured to determine the position of the closest of said plurality of second sensors to the weld line, and to activate said closest sensor to scan for flaws in the tubular.

* * * * *